US00PP13087P2

(12) United States Plant Patent
Zary

(10) Patent No.: US PP13,087 P2
(45) Date of Patent: Oct. 15, 2002

(54) HYBRID TEA ROSE PLANT NAMED 'JACMPIAD'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/779,302

(22) Filed: Feb. 7, 2001

(65) Prior Publication Data

US 2002/0108154 P1 Aug. 8, 2002

(51) Int. Cl.[7] ..... A01H 5/00

(52) U.S. Cl. ..... Plt./130

(58) Field of Search ..... Plt./139, 132, 130

*Primary Examiner*—Bruce R. Campell
*Assistant Examiner*—June Hwu
(74) *Attorney, Agent, or Firm*—Klarquist Sparkman, LLP

(57) ABSTRACT

A hybrid tea rose plant characterized by its vigorous, upright growth and glossy, dark green foliage; and its high centered, large flowers, the petals of which have a novel blend of red shades of color.

1 Drawing Sheet

BOTANICAL CLASSIFICATION

*Rosa hybrida* 'JACmpiad'.

The present invention relates to a new and distinct variety of rose plant of the hybrid tea class which was originated by me by crossing the variety MACauck, U.S. Plant Pat. No. 5,519, with an unnamed seedling.

The primary objective of this breeding was to produce a new rose variety having the long stems, high centered flower form and vigorous growth of the female parent combined with the large flowers, glossy foliage and disease resistance of the coral pink flowered hybrid tea male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright growth;
2. Glossy, dark green foliage;
3. High centered large flowers;
4. Novel blend of colors on the petals; and
5. Resistance to rust and powdery mildew.

Asexual reproduction of this new variety by budding on Dr. Huey understock, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—MACauck (U.S. Plant Pat. No. 5,519).
*Pollen parent.*—Unnamed (Unnamed×Unnamed).
Classification:
*Commercial.*—Hyrid tea.

FLOWER

Observations made from specimens grown in a garden environment at Somis, Calif., two years of age in January, 1999 to November, 2000.

Blooming habit: Continuous.
Bud:
*Size.*—About 1¾ inches long when the petals start to unfurl.
*Form.*—The bud form is long, pointed ovoid.
*Color.*—When sepals first divide, bud color is Red Group 45C as sepals crack. As the sepals drop, the outer 85% of the petal is Red Group 45C. The inner 15% is Red Group 45D except along the midrib where it remains Red Group 45C. When half blown, the upper sides of the petals are Red Group 45C on the petal margin changing to Red Group 45D. The base of the petal has a large half moon (½"×½") of Yellow Group 4D. The lower sides of the petals are Red Group 45C on petal margin; the rest of the petal surface is Red Group 45D fading in the center of petal toward Red Group 55D with veins showing clearly. Veins are slightly darker in color.
*Sepals.*—Color: Green Group 138B. Surface texture: Covered in fine hairs. There are three normally to heavily appendaged sepals. There are two unappendaged sepals with hairy edges. Length: 1¾–2¼ inches; Width: ¾ inch.
*Receptacle.*—Color: Yellow-Green Group 146B. Shape: Funnel. Size: Medium (¼"×¼"). Surface: Smooth.
*Peduncle.*—Length: Medium, averaging about 3½ inches. Surface: Smooth. Color: Yellow-Green Group 146B except when exposed to bright sunlight. Then it is close to Greyed-Red Group 178B. Strength: Stiff, erect.

Bloom:

*Size*.—Large. Average open size is 4½ inches.

*Borne*.—Singly.

*Stems*.—Strength: Strong. Average length is about 16–18 inches.

*Form*.—When first open: High centered. Permanence: Retains Retains its form to the end, outer petals curl back.

*Petalage*.—Number of petals under normal conditions: 30.

*Color*.—The upper sides of the petals are Red Group 45C on the petal margin changing to Red Group 45D over the rest of the petal. The base of the petal has a large half moon (½"×½") of Yellow-Group 4D. The reverse sides of the petals are Red Group 45C on the petal margin. The rest of the petal surface is Red Group 45D fading in the center of the petal toward Red Group 55D with veins showing clearly. Veins are slightly darker in color. The base of each petal has a small area about ⅛"×⅛" of Yellow Group 7C on the upper petal surface and Yellow Group 5D on the lower petal surface. The major color on the upper side is Red Group 45D.

*Variegations*.—None.

*Discoloration*.—The general tonality at the end of the first day: No change. At the end of the third day: No change. By day 4 or 5, as the petals unfold, the upper surface color deepens and spreads on the petal surface until at petal drop, the entire surface, except for the large area of Yellow Group 4D, becomes Red Group 45C. The lower surface stays unchanged through petal drop.

*Fragrance*.—Slight. (Too slight to characterize).

Petals:

*Texture*.—Thick, leathery.

*Shape*.—Round.

*Form*.—Tips slightly recurved.

*Arrangement*.—Imbricated. There are no petaloids in the center.

*Persistence*.—Petals drop off cleanly before drying.

*Lastingness*.—On the plant: Fair (about 5–7 days). As a cut flower: Fair (about 7 days).

Reproductive parts:

*Stamens*.—Number: 80–100. Length: 9/16 inch. Anthers: Length: ⅛ inch. Color: Yellow-Orange Group 16C. Arrangement: Regular around styles. Filaments: Color: Yellow Group 8B. Length: 7/16 inch. Pollen: Color: Yellow-Orange Group 16C.

*Pistils*.—Number: 50–70. Length: 7/16 inch. Styles: Color: Green-White Group 157D. Length: 5/16 inch. Stigmas: Color: Yellow-White Group 158B. Length: ⅛ inch.

Plant:

*Form*.—Bush.

*Growth*.—Vigorous. At maturity, height is 6 feet, width is 4 feet, in Somis, Calif.

Foliage: Number of leaflets on normal mid-stem leaves: 5.

*Size*.—Large (6 inches long×5 inches wide).

*Quantity*.—Abundant.

*Color*.—New foliage: Upper surface: Greyed-Red Group 178A. Lower surface: Greyed-Red Group 178A. Old foliage: Upper surface: Green Group 136A. Lower surface: Green Group 138B.

Leaflets:

*Shape*.—Pointed oval. Base: Oblique. Apex: Acuminate.

*Texture* .—Leathery, glossy.

*Edge*.—Serrated.

*Serration*.—Single, small.

*Petiole rachis*.—Color: Yellow-Green Group 147D.

*Petiole underside*.—Smooth with an occassional prickle.

*Stipules*.—Length: about ½ inch. Color: Yellow-Green Group 147D.

*Disease resistance*.—Susceptible to mildew and blackspot, resistant to rust under normal growing conditions.

Wood:

*New wood*.—Color: Yellow-Green Group 147B often with areas of Greyed-Purple Group 184A. Bark: Smooth.

*Old wood*.—Color: Green Group 138B. Bark: Smooth.

Prickles:

*Quantity*.—On main canes from base: Ordinary. On laterals from main canes: Ordinary.

*Form*.—Medium, hooked downward.

*Length*.—13/32 inch.

*Color when young*.—Greyed-Purple Group 183A.

*Color when mature*.—Greyed-Orange Group 173C.

Small prickles:

*Quantity*.—On main stalks: None. On laterals: None.

Plant hardiness: Winter hardy to Zone 5.

I claim:

1. A new and distinct variety of rose plant of the bybrid tea class, substantially as herein shown and described, characterized particularly as to novelty by its vigorous, upright growth and glossy, dark green foliage; and its large, high centered flowers, the petals of which have a novel blend of red shades of color.

* * * * *

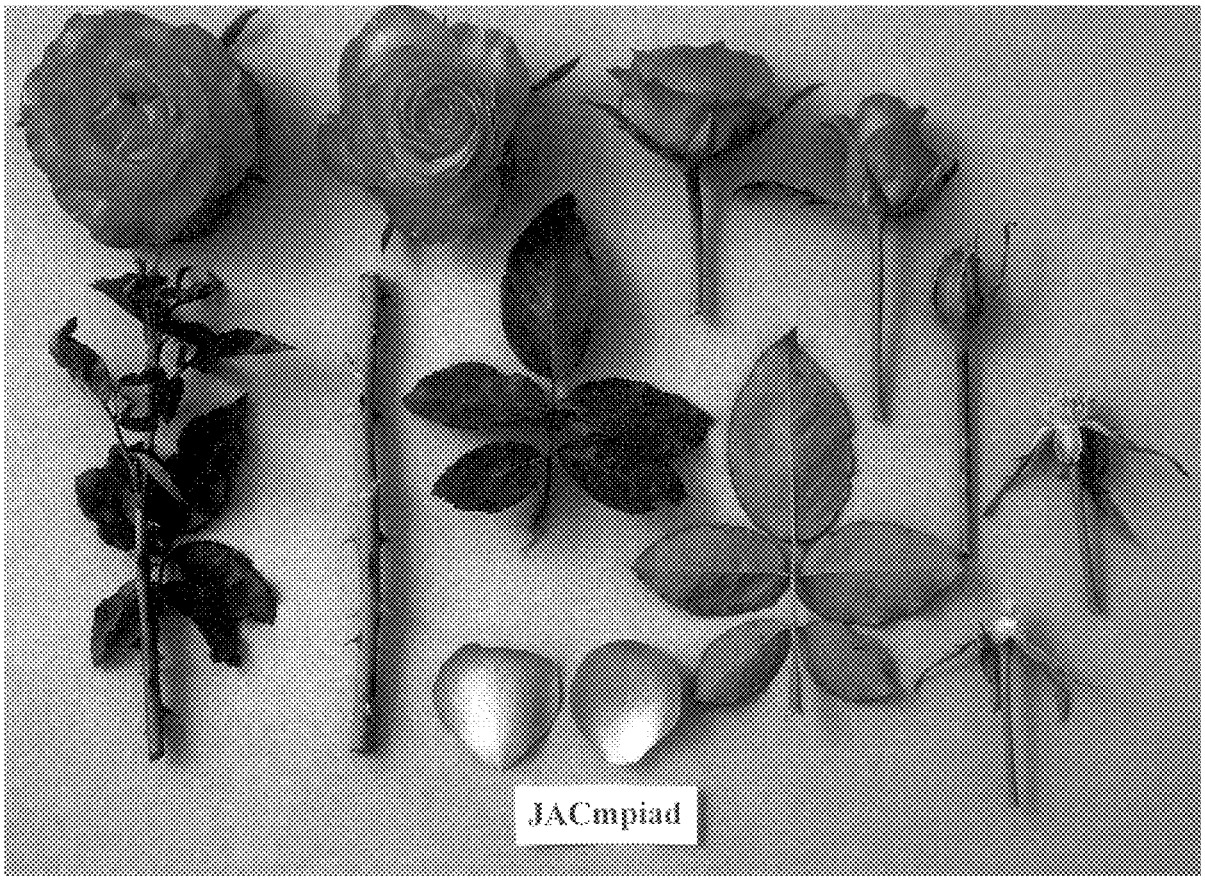
JACmpiad